United States Patent
Dam-Huisman (10) Patent No.: US 11,738,135 B2
(45) Date of Patent: Aug. 29, 2023

(54) PRESSURE CONTROL UNIT FOR AN OPHTHALMIC SURGICAL SYSTEM

(71) Applicant: Crea IP B.V., Vierpolders (NL)

(72) Inventor: Adriaantje Coliene Dam-Huisman, Delfgauw (NL)

(73) Assignee: Crea IP B.V., Vierpolders (NL)

( * ) Notice: Subject to any disclaimer, the term of this patent is extended or adjusted under 35 U.S.C. 154(b) by 122 days.

(21) Appl. No.: 16/762,418

(22) PCT Filed: Oct. 23, 2018

(86) PCT No.: PCT/NL2018/050699
§ 371 (c)(1),
(2) Date: May 7, 2020

(87) PCT Pub. No.: WO2019/093880
PCT Pub. Date: May 16, 2019

(65) Prior Publication Data
US 2021/0187173 A1    Jun. 24, 2021

(30) Foreign Application Priority Data
Nov. 10, 2017   (NL) ...................... 2019884

(51) Int. Cl.
*A61M 1/00* (2006.01)
*A61F 9/007* (2006.01)
(Continued)

(52) U.S. Cl.
CPC ............ *A61M 1/743* (2021.05); *A61F 9/007* (2013.01); *A61M 1/772* (2021.05);
(Continued)

(58) Field of Classification Search
CPC ................ A61F 9/007; A61M 39/223; A61M 2205/3331; A61M 2210/0612;
(Continued)

(56) References Cited

U.S. PATENT DOCUMENTS 3,902,495 A * 9/1975 Weiss .................. A61M 3/0212
606/128
5,094,260 A * 3/1992 Stuart ................ G05D 16/2053
137/596.17
(Continued)

FOREIGN PATENT DOCUMENTS

CN       106474577 A  *  3/2017

*Primary Examiner* — Catharine L Anderson
*Assistant Examiner* — Linnae E. Raymond
(74) *Attorney, Agent, or Firm* — N.V. Nederlandsch Octrooibureau (57) ABSTRACT

Pressure control unit for an ophthalmic irrigation/aspiration system having a chamber with an upper part for storing air and a lower part for storing a surgical fluid to be irrigated or aspirated, the pressure control unit including a negative pressure source, a positive pressure source and an adjustable valve arrangement. The adjustable valve arrangement includes a vacuum port connected to the negative pressure source and a pressure port connected to the positive pressure source. The adjustable valve arrangement also includes a main port in controllable fluid communication with the vacuum port and the pressure port and the main port is connected to an upper part of the chamber.

14 Claims, 5 Drawing Sheets

(51) Int. Cl.
*A61M 39/22* (2006.01)
*A61M 3/02* (2006.01)

(52) U.S. Cl.
CPC ..... *A61M 39/223* (2013.01); *A61B 2217/005* (2013.01); *A61B 2217/007* (2013.01); *A61M 1/82* (2021.05); *A61M 3/0254* (2013.01); *A61M 2039/226* (2013.01); *A61M 2205/3334* (2013.01); *A61M 2205/3341* (2013.01); *A61M 2205/7518* (2013.01); *A61M 2210/0612* (2013.01)

(58) Field of Classification Search
CPC ...... A61M 1/77; A61M 1/772; A61M 1/0058; A61M 1/0062
See application file for complete search history.

(56) References Cited

U.S. PATENT DOCUMENTS

| | | | |
|---|---|---|---|
| 5,354,268 A * | 10/1994 | Peterson | A61M 1/80 604/35 |
| 5,674,194 A | 10/1997 | Jung et al. | |
| 2007/0083150 A1 | 4/2007 | Nazarifar et al. | |
| 2009/0099498 A1 | 4/2009 | Demers et al. | |
| 2015/0250939 A1* | 9/2015 | Kuntz | A61M 1/82 604/28 |
| 2017/0224429 A1* | 8/2017 | Fung | A61B 90/08 |
| 2017/0273826 A1* | 9/2017 | Sanchez, Jr. | A61F 9/0017 |

* cited by examiner

PRESSURE CONTROL UNIT FOR AN OPHTHALMIC SURGICAL SYSTEM

FIELD OF THE INVENTION

The present invention relates to a pressure control unit, in particular a pressure control unit for use in an aspiration/irrigation system, such as an ophthalmic aspiration/irrigation system. In a further aspect the present invention relates to a method for regulating the pressure in an ophthalmic aspiration/irrigation system.

BACKGROUND ART

During ophthalmic surgery, fluid is typically delivered into the eye and aspirated therefrom. Generally, a pressure source is used to move fluid to the eye and a pressure source or flow drain to move fluid from the eye. For aspiration procedures, a negative pressure may be employed to draw fluid from the eye into an aspiration chamber. For irrigation procedures, positive pressure is applied to deliver fluid from an infusion source to the eye.

US patent publication U.S. Pat. No. 5,674,194 discloses a pressure control unit configured to generate a vacuum for a suction probe of which a desired vacuum level can be manipulated by an input device of the pressure control unit. The system comprises a regulated high pressure source connected via an input manifold to a proportional valve, wherein the degree to which the proportional valve is open determines the pressure and air flow rate through a venturi connected to an output of the proportional valve. The pressure control unit further comprises a cassette volume connected to the suction probe and to the venturi, wherein the venturi allows a vacuum to be drawn at the suction probe.

SUMMARY OF THE INVENTION

The present invention seeks to provide an improved pressure control unit for an ophthalmic surgical system, such as an ophthalmic aspiration/irrigation system, wherein the pressure control unit minimizes air consumption and circumvents the use of an external air source. The pressure control unit of the present invention further aims to provide fast pressure control of aspiration or irrigation pressure with maximum precision.

According to an aspect of the present invention, there is provided a pressure control unit for an aspiration/irrigation system having a chamber with an upper part for storing air and a lower part for storing a surgical fluid to be irrigated or aspirated. The pressure control unit comprises a negative pressure source, a positive pressure source and an adjustable valve arrangement, wherein the adjustable valve arrangement comprises a vacuum port connected to the negative pressure source and a pressure port connected to the positive pressure source. The adjustable valve arrangement further comprises a main port in controllable fluid communication with the vacuum port and the pressure port, wherein the main port is connected to the chamber.

The adjustable valve arrangement is adapted to control the air pressure and air flow to and from the chamber through the main port corresponding to the intensity at which the negative pressure source and/or the positive pressure source is/are allowed to be active and supply the negative pressure and/or positive pressure to the vacuum port and pressure port, respectively. In other words the amount of opening ratio of each valve in the adjustable valve arrangement determines their individual contribution and as such the coupling between the pressure sources and the main port.

Since regulating the pressure within the chamber is achieved through both negative and/or positive pressure sources (negative and positive pressure being used with respect to an ambient pressure), the pressure control unit of the present invention is able to provide dynamic pressure control within the chamber with exceptionally short response times and precision, wherein the adjustable valve arrangement is configured to provide any required pressure to the chamber during an ophthalmic procedure.

Another advantage of the pressure control unit is that it is conveniently configured to connect to, for example, an existing chamber, which may be a disposable chamber, of an ophthalmic aspiration/irrigation system. In this way an ophthalmic surgical system can be upgraded using the pressure control unit for increasing irrigation and/or aspiration response times as well as increased accuracy at which required pressures can be provided to the chamber.

According to a further aspect of the present invention, there is provided a method for regulating the pressure in an ophthalmic surgical system comprising a chamber for exchanging surgical fluid and a pressure control unit having a negative pressure source, a positive pressure source and an adjustable valve arrangement, the valve arrangement comprising a vacuum port connected to the vacuum source and a pressure port connected to the pressure source, and wherein the valve arrangement further comprises a main port configured for fluid communication with the chamber; wherein the method comprises the steps of determining a desired chamber pressure; delivering the desired pressure to the chamber via the main port; measuring the pressure within the chamber; adjusting the adjustable valve arrangement to deliver positive and/or negative pressure to maintain the desired pressure within the chamber.

SHORT DESCRIPTION OF DRAWINGS

The present invention will be discussed in more detail below, with reference to the attached drawings, in which.

DESCRIPTION OF EMBODIMENTS

Exemplary embodiments of the present invention will now be described in detail. The skilled person will understand that devices and methods described herein are non-limiting exemplary embodiments and that the scope of protection is defined by the claims. For example, although the present invention is described with respect to ophthalmic aspiration and/or irrigation procedures, the skilled person readily understands that the present invention may be used in other applications, for example in other aspiration and/or irrigation systems, e.g. fine needle aspiration procedures. The skilled person will also understand that the features illustrated or described in connection with one exemplary embodiment may be combined with features described in other exemplary embodiments. Such modifications and variations are included within the scope of the present disclosure.

Figure 1:
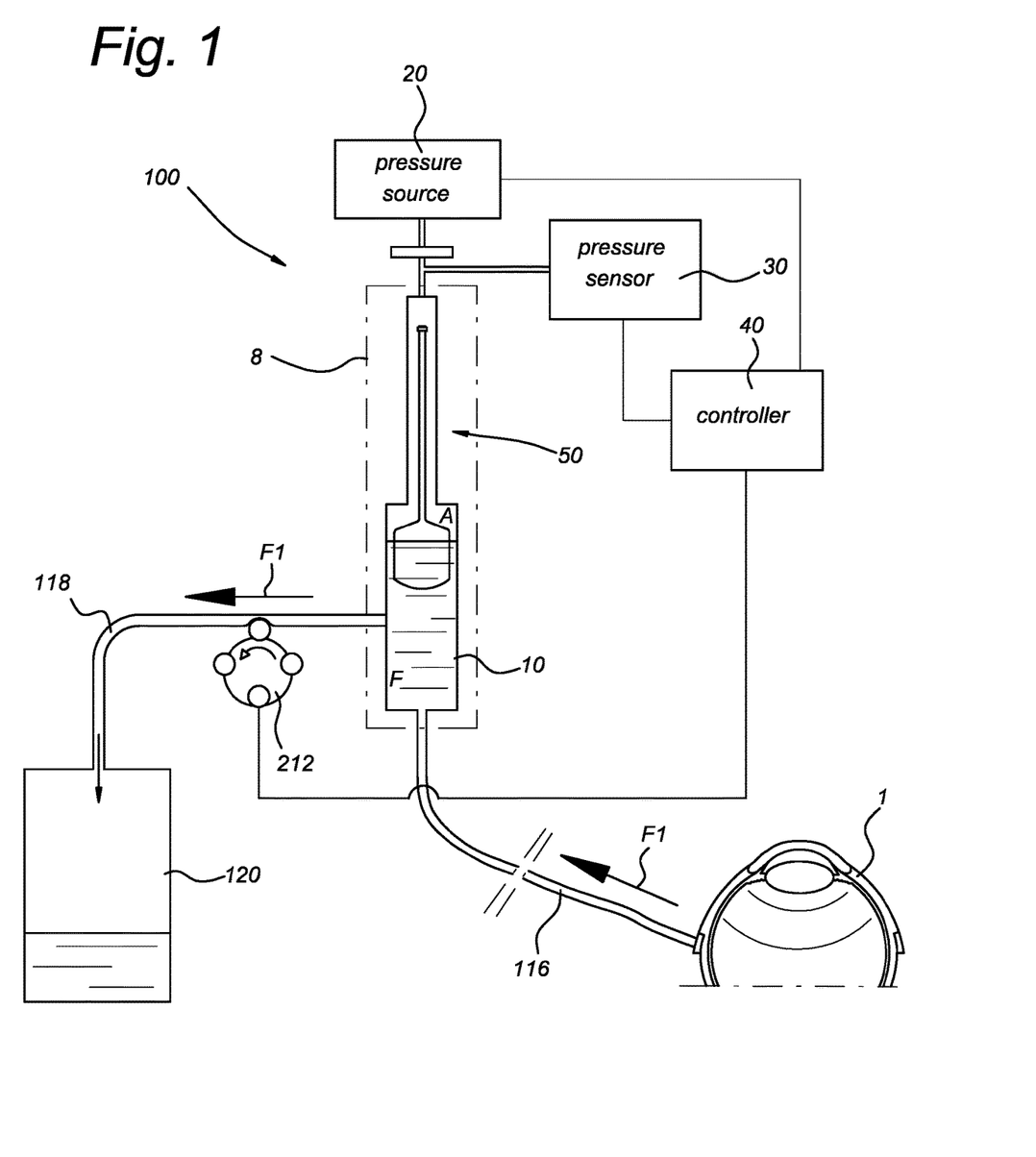
FIG. 1 shows an embodiment of an aspiration system for aspirating ocular material during an ophthalmic surgical procedure.
Figure 2:
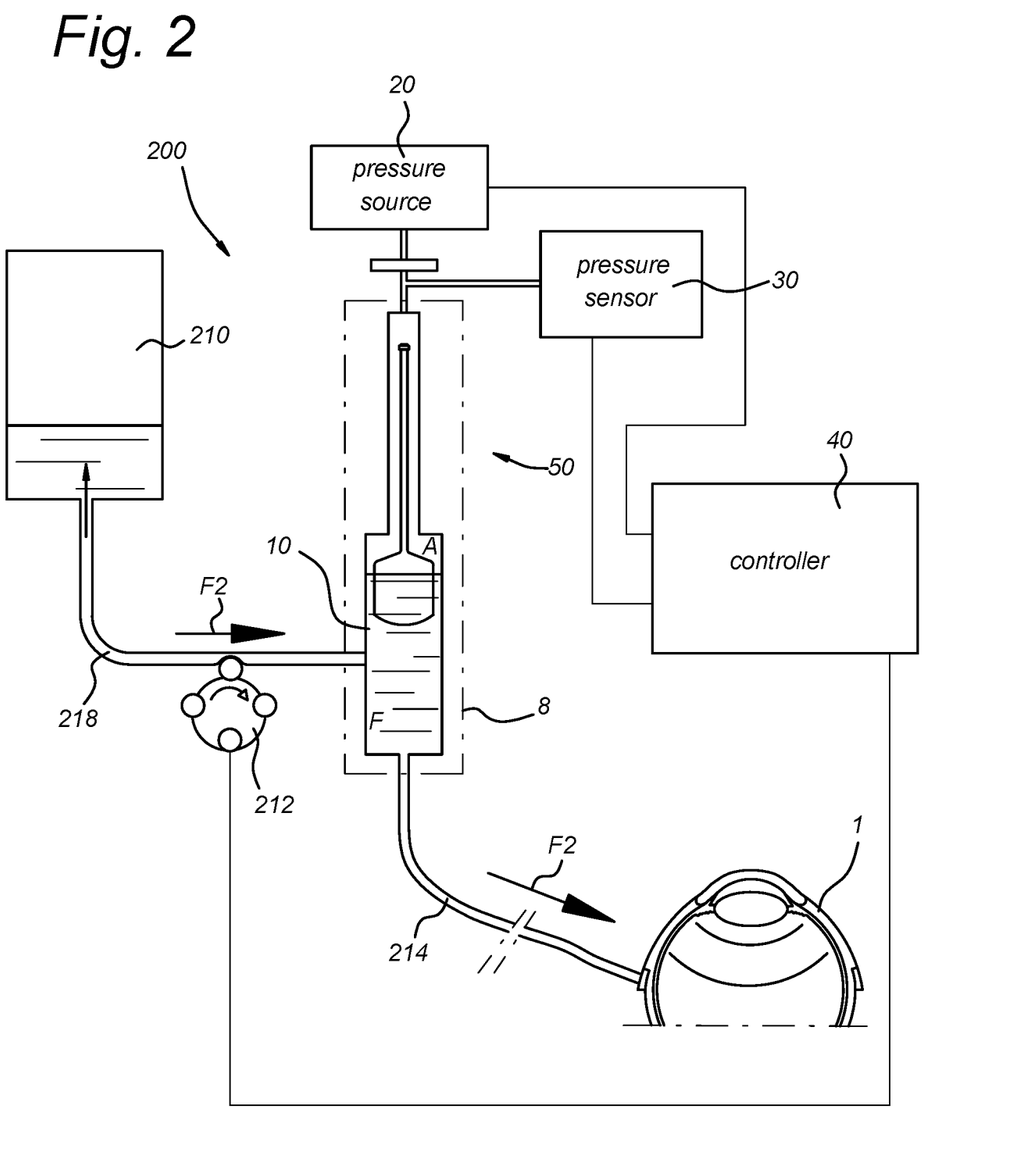
FIG. 2 shows an embodiment of an irrigation system for irrigating the eye during an ophthalmic surgical procedure.

The pressure control unit according to the present invention may be employed in an exemplary embodiment of an aspiration system 100 shown in FIG. 1 or in an exemplary embodiment of an irrigation system 200 as shown in FIG. 2. As shown, the aspiration system 100 and the irrigation system 200 according to embodiments of the present invention each comprise a cassette 8, sometimes referred to as a surgical cassette, having a chamber 10. The chamber 10 is configured to store a fluid F in a lower part 10b of the chamber 10 and air A in an upper part 10a of the chamber 10, the upper part 10a being the remaining space at the top of the chamber 10 (see also the description of FIGS. 4A and 4B below).

A variable pressure source 20 is coupled to the chamber 10 to control the pressure within the chamber 10 and thus the flow of fluid between the chamber 10 and an eye 1 of a patient. The skilled person in the art will appreciate that in the aspiration system 100 shown in FIG. 1 the variable pressure source 20 is at least capable of applying a negative pressure to the chamber 10 to draw fluid from the eye 1 into the chamber 10 via an aspiration line 116, i.e. fluid moves in the direction of arrow F1 in FIG. 1.

In an irrigation system 200, the variable pressure source 20 is at least capable of applying a positive pressure to the chamber 10 to deliver fluid from the chamber 10 to the eye 1 via an irrigation line 214, i.e. fluid moves in the direction of arrow F2 in FIG. 2. Of course, a variable pressure source 20 capable of applying a positive pressure and a negative pressure to the chamber 10 is advantageously versatile and can be used in both irrigation and aspiration procedures. The cassette 8 as depicted in FIGS. 1 and 2 may further comprise a pressure sensor 30 which is in fluid communication with the chamber 10 to monitor the air pressure within the chamber 10.

The aspiration system 100 and the irrigation system 200 typically comprise a pump 212 that controls the egress and ingress of fluid F from the chamber 10. The pump 212 may be any pump suitable for this purpose, such as a peristaltic pump of any type known in the art. The skilled person will appreciate that in an aspiration system 100 as shown in FIG. 1, the pump 212 is configured to deliver aspirated fluid from the chamber 10 to a drain 120, which is coupled to the chamber 10 by way of a drainage line 118. In the irrigation system shown in FIG. 2, the pump 212 is configured to deliver irrigation fluid from an infusion bottle 210 to the chamber 10 by way of an infusion line 218. The cassette 8 also comprises a fluid level indicator 50 to indicate the level of fluid F within the chamber 10.

As shown in FIG. 2, a controller 40 may be provided in communication with the variable pressure source 20, pressure sensor 30, the fluid level indicator 50, and the pump 212. The controller 40 is configured to control the pressure and the fluid level within the chamber 10 based on, for example, measurements taken by the pressure sensor 30 and/or the fluid level indicator 50, and by controlling a velocity of the pump 212. Note that the controller 40 can likewise be provided to the aspiration system 100 of FIG. 1 and connected to the variable pressure source 20, pressure sensor 30, pump 212 and the fluid level indicator 50 to control the pressure and the fluid level within the chamber 10.

Figure 3:
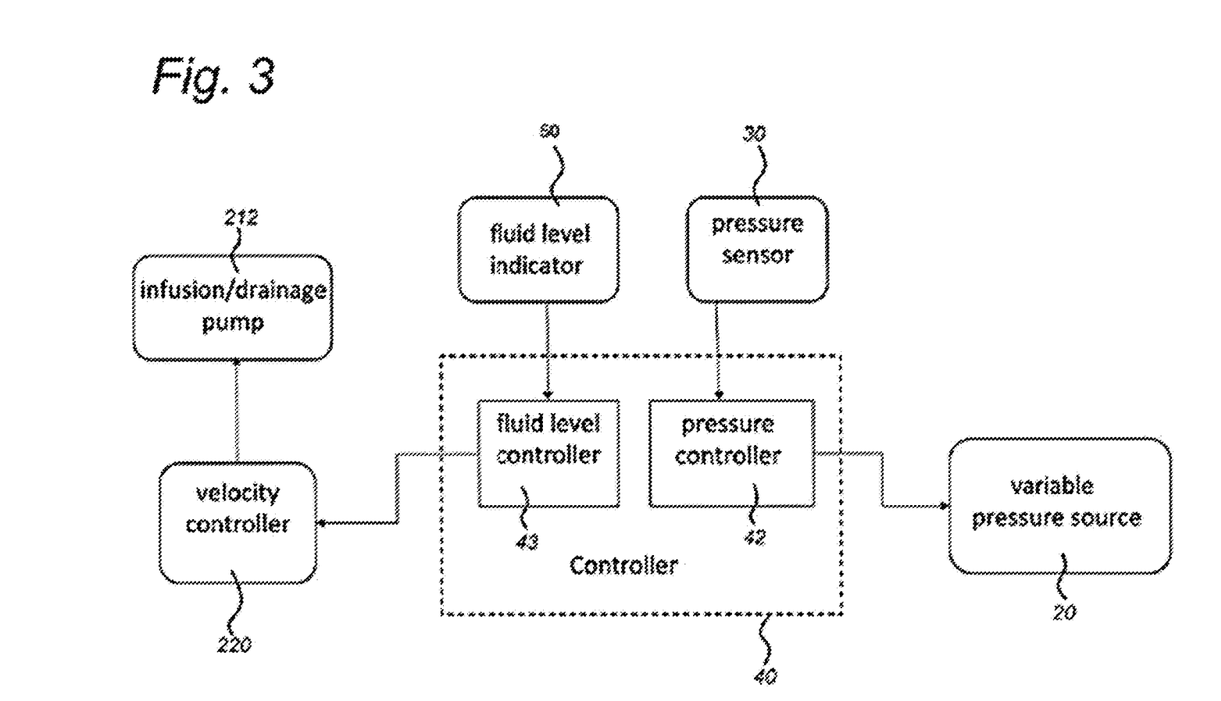
FIG. 3 shows a schematic view of a controller for use in an ophthalmic aspiration/irrigation system.

Referring now to the schematic of FIG. 3, in an embodiment the controller 40 comprises a fluid level controller 43 for maintaining the fluid level within chamber 10 within a desired range and a pressure controller 42 for maintaining a desired pressure within the chamber 10. The desired pressure within the chamber 10 is a negative or positive pressure depending on whether aspiration or irrigation is needed.

The fluid level controller 43 receives fluid level information from the fluid level indicator 50 and provides a set-point to a velocity controller 220, which controls the pump 212 to maintain the fluid level within chamber 10 within a desired range. For example, in aspiration applications the velocity controller 220 controls the rate at which fluid F is drained from the chamber 10 into the drain 120. If the controller 40 determines based on feedback from the fluid level indicator 50 that the fluid level within the chamber 10 is too high, the controller 40 adjusts the set point of the velocity controller 220 to increase the rate/speed at which pump 212 moves fluid F from the chamber 10 to the drain 120.

In irrigation applications, the velocity controller 220 controls the rate at which fluid F enters the chamber 10 from the infusion bottle 210. If, based on feedback from the fluid level indicator 50, the controller 40 determines that the fluid level within the chamber 10 is too low, the controller 40 adjusts the set-point of the velocity controller 220 to increase the rate/speed at which pump 212 delivers irrigation fluid from the infusion bottle 210 to the chamber 10.

The pressure controller 42 receives pressure information from the pressure sensor 30 and adjusts the pressure delivered by the variable pressure source 20 to maintain the pressure within the chamber 10 at the desired level.

Advantageously, the controller 40 shown in FIG. 3 can also allow for calculation of the flow rate to and from the eye 1 without the need for a flow sensor within the aspiration line 116 or the irrigation line 214. This is advantageous because ophthalmic surgical systems generally comprise narrow gauge irrigation/aspiration lines, across which accurate flow sensing can be challenging. However, in the aspiration and irrigation systems 100, 200 described above, the controller 40 may calculate the flow rate to or from the eye 1 based on all or some of the following known quantities: the fluid level within the chamber (measured by fluid level indicator 50); the pressure within chamber 10 (measured by pressure sensor 30); and the flow rate dictated by the pump 212 to and from the chamber 10, system parameters relevant for pressure losses in the flow to/from the eye during use (e.g. tubing and needle length and diameters).

The above description of FIG. 3 relates to a pressure mode of operation, wherein a user can input a set point for the desired pressure to pressure controller 42. This may be applied both when the present invention embodiments are used for controlling irrigation to the eye, and for controlling aspiration from the eye. In a further embodiment, specifically suited for aspiration purposes, the present invention embodiments are operated in a flow control mode. In the flow control mode, a set point for the desired aspiration flow is input to the velocity controller 220, for controlling the speed of the drainage pump 212. The fluid level controller 43 uses the input from the fluid level indicator 50 to provide a pressure set point to the pressure controller 42 that subsequently control the variable pressure source 20 to ensure the fluid level is controlled to an internal defined set point.

It will be appreciated that to allow precise control of the pressure within the eye 1, the variable pressure source 20 should be capable of providing fast pressure control with maximum precision within the chamber 10. To that end reference is made to FIGS. 4A and 4B, each of which show an embodiment of a pressure control system 21 for an ophthalmic irrigation and aspiration system 100, 200 having a chamber 10 with a lower part 10b for storing a surgical fluid F to be irrigated or aspirated.

Figure 4A:
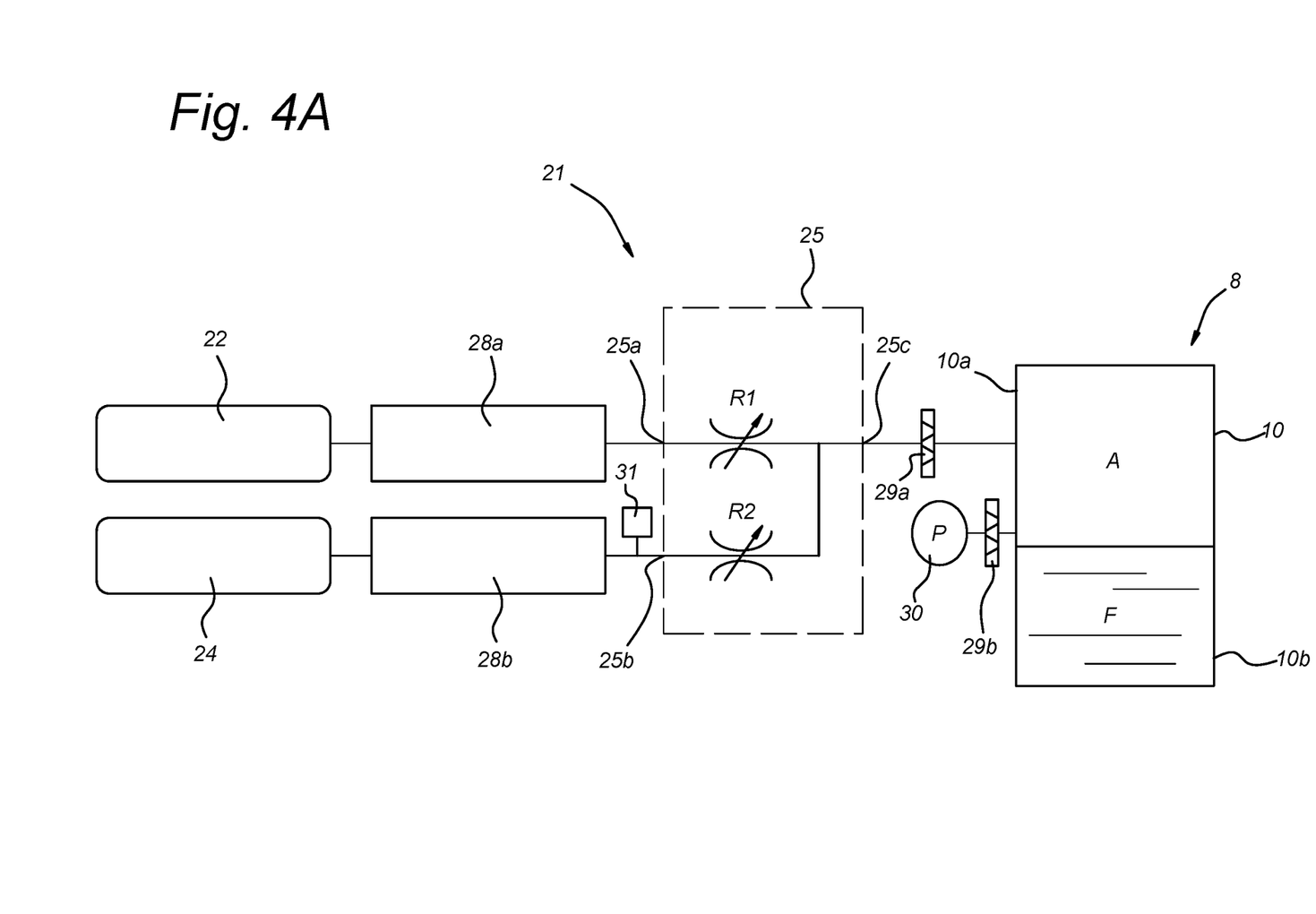
FIGS. 4A and 4B each show a schematic view of a pressure control unit for an ophthalmic aspiration/irrigation system according to an embodiment of the present invention.
Figure 4B:
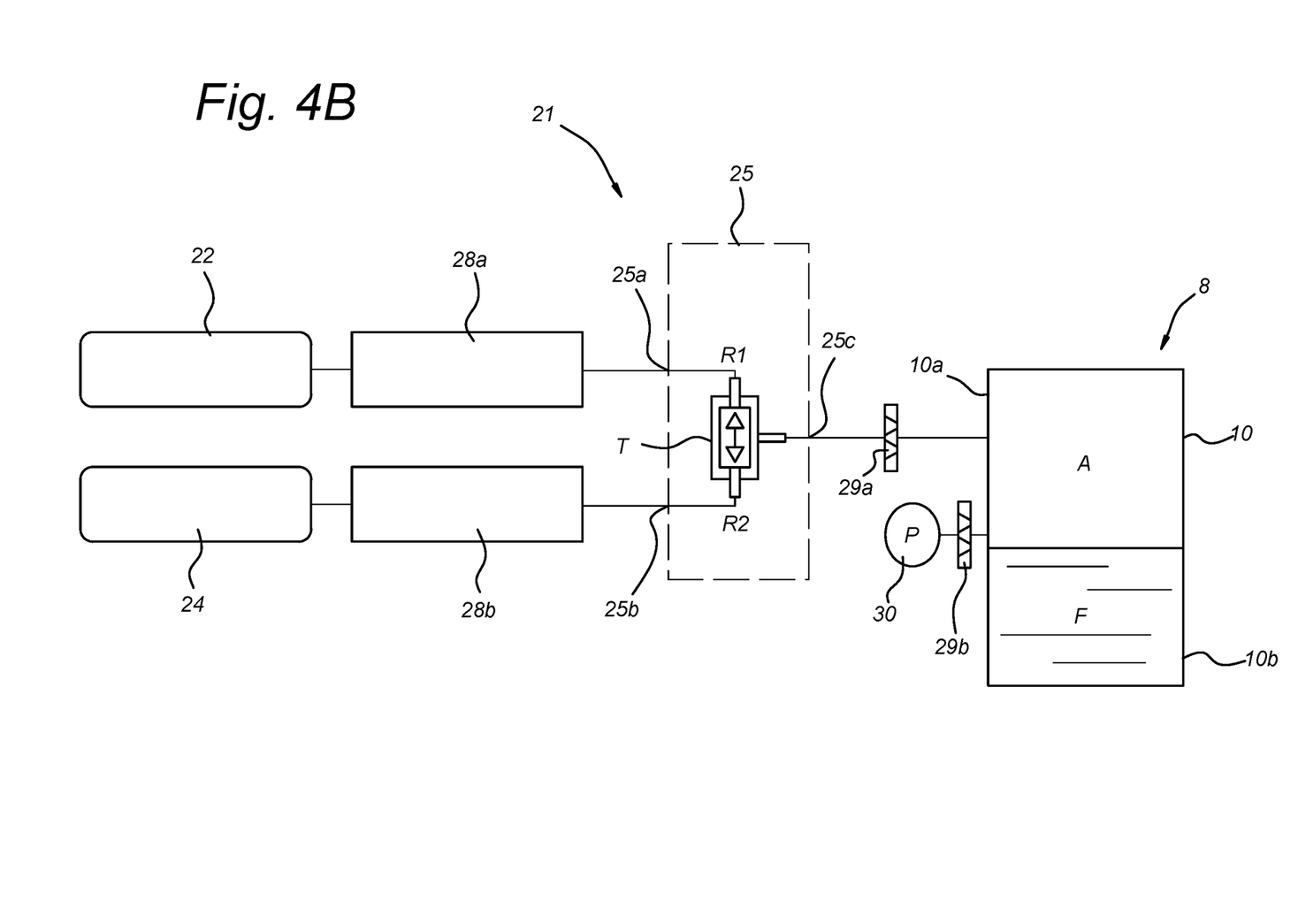

According to the present invention, the pressure control unit 21 comprising a negative pressure source 22 (e.g. a vacuum source) and a positive pressure source 24 (e.g. a compressor). In an embodiment, the negative or positive pressure source 22, 24 is a membrane pump for example, although the skilled person will appreciate that other positive and/or negative pressure sources could be employed. The terms negative and positive pressure are being used herein with respect to an ambient pressure. As an alternative implementation one of the pressure sources 22, 24 could be actually at the ambient pressure.

The pressure control unit 21 is further provided with an adjustable valve arrangement 25, wherein the valve arrangement 25 comprises a vacuum port 25a connected to the negative pressure source 22 and a pressure port 25b connected to the positive pressure source 24. The adjustable valve arrangement 25 also comprises a main port 25c in controllable fluid communication with the vacuum port 25a and the pressure port 25b, wherein the main port 25c is connected to a chamber 10, e.g. connected to the chamber 10 (more particularly to an upper part 10a of the chamber 10), for storing air A. As mentioned above, the chamber 10 is configured for storing and exchanging a surgical fluid F stored in a lower part 10b of the chamber 10.

The adjustable valve arrangement 25 is adapted to control the flow of air to/from the chamber 10 through the main port 25c corresponding to the intensity at which the vacuum source 22 and/or the pressure source 24 is/are active. Since the valve arrangement 25 shown in FIGS. 4A and 4B couples the chamber 10 to a negative pressure source 22 as well as a positive pressure source 24, the pressure control unit 21 is able to provide fast, dynamic pressure control within chamber 10 with remarkable precision. The adjustable valve arrangement 25 of the present invention is thus configured to provide virtually any pressure within the chamber 10 at any desired speed and accuracy. Factors influencing the speed and accuracy are the total air volume A and the presence (or absence) of a restriction (such as optional filter 29a. It is noted that the present application embodiments could also be used to control pressure in an infusion bottle instead of in the chamber 10 of the cassette 8.

In an embodiment, the adjustable valve arrangement 25 is a proportionally adjustable valve arrangement allowing smooth and continuous changes in air pressure and air flow across the main port 25c. The proportionally adjustable valve arrange arrangement is capable of switching between and/or "blending" the negative and positive pressure sources 22, 24, so that any desired pressure and air flow across the main port 25c can be achieved with great speed and precision. As an alternative implementation, a pulse width modulation (PWM) controlled on/off valve arrangement may be applied.

In an exemplary embodiment as shown in FIG. 4A, the adjustable valve arrangement 25 comprises a first adjustable valve R1 connected between the vacuum port 25a and the main port 25c and a second adjustable valve R2 is connected between the pressure port 25b and the main port 25c. This allows accurate selection and control of both negative pressure and positive pressure at the main port 25c, so that any desired pressure within the chamber 10 can be reached fast and accurately maintained (within the negative and positive pressure ranges of the vacuum source 22 and/or pressure source 24).

In an advantageous embodiment, the first adjustable valve R1 is a first proportional valve and the second adjustable valve R2 is a second proportional valve. Each of the proportional valves R1, R2 allow for fast, continuous control to further increase speed and accuracy of the air flow across the main port 25c.

Controlling the first and second adjustable/proportional valves R1, R2 with e.g. a current source can be advantageous because current controlled valves may be less sensitive for temperature variations when compared to voltage controlled valves. Alternatively, the first and second adjustable/proportional valves R1, R2 are position controlled valves.

In a further embodiment, the first and second adjustable/proportional valves R1, R2 are biased with a first current to allow a bias flow in the flow path between negative pressure source 22 and positive vacuum source 24, whilst maintaining a net zero flow through the main port 25c (keeping pressure in the chamber 10 at a constant level). In general, the current/flow characteristic of such a valve includes a threshold current below which the valve remains closed. Biasing the first and second adjustable/proportional valves R1, R2 with a current at least equal to this threshold current allows to have a faster response time when further opening one of the valves R1, R2 during control.

To allow control and proper setting of the adjustable valve arrangement 25, the pressure control unit may further comprise a flow sensor 31 arranged in a bias flow path between the negative pressure source 22 and the positive pressure source 24. The bias flow path comprises the direct connection parts between the negative pressure source 22 and the positive pressure source 24 in any of the exemplary embodiments described herein. E.g. the flow sensor 31 is arranged between the positive pressure source 24 and the pressure port 25b or between the vacuum source 22 and the vacuum port 25a. The flow sensor 31 can be any suitable flow sensor, e.g. an in-line flow sensor.

The flow sensor 31 may be connected to the controller 40 (or to a dedicated controller), and may be implemented as a mass flow sensor or as a volumetric flow sensor (e.g. a differential pressure based flow sensor which allows measuring a volumetric flow rate by measuring a differential pressure over a (fixed) restriction). The measurement data from the flow sensor 31 can then be used in a secondary control loop which actively controls the flow in the bias flow path (without affecting flow through the main port 25c).

Referring to FIG. 4B, in an alternative embodiment, the adjustable valve arrangement 25 is a three-way valve arrangement T, which may be seen as a single, unitary valve manifold having three connecting ports and a valve insert adapted to control/divide air flow through and among these three connecting ports. For example, the three-way valve arrangement (T) may be seen as a single valve unit comprising the vacuum port 25a, the pressure port 25b, and the main port 25c to accurately control the degree in which the vacuum port 25a and/or the pressure port 25b communicate with the main port 25c.

As with the first and second adjustable/proportional valves R1, R2, the three-way valve arrangement T may be current controlled, thereby reducing or avoiding temperature dependent valve sensitivities. Note that the skilled person in the art will appreciate that voltage control may still be effectively applied to control the adjustable valve arrangement 25, in particular the first and second adjustable/proportional valves R1, R2 as well as a three-way valve arrangement T as described above.

In order to monitor the pressure within the chamber 10, an embodiment is provided wherein the pressure control unit 21 comprises a pressure sensor 30 in communication with the main port 25c. For example, in an embodiment the pressure sensor 30 is connected to a conduit arranged between the main port 25c and the chamber 10. In an alternative embodiment the pressure sensor 30 may be directly connected to the upper part 10a of the chamber 10 as depicted in FIGS. 4A and 4B via a separate conduit. As mentioned earlier, a controller 40, see e.g. FIGS. 2 and 3, can be provided and configured to adjust the adjustable valve arrangement 25 to maintain a desired pressure in the chamber 10 in response to the pressure measured by the pressure sensor 30.

During a surgical procedure, the pressure sensor 30 provides feedback to the controller 40 for adjusting the valve arrangement 25 to maintain the pressure within chamber 10 at a desired level. For example, if the sensed pressure within the chamber 10 is lower than a required pressure, the pressure can be quickly increased by adjusting the valve arrangement 25 to deliver pressurised air from the positive pressure source 24 to the main port 25c and thus to the chamber 10. Should the sensed pressure within the chamber 10 be higher than the required pressure, the pressure can be quickly decreased by adjusting the valve arrangement 25 such that a negative pressure is applied to the main port 25c and thus to the chamber 10. This allows for rapid adjustment of the pressure within the chamber 10. This may also be advantageous as it allows to deal with blockages and/or leaks within the ophthalmic aspiration/irrigation system 100, 200.

In an embodiment, the controller 40 controls the first and second adjustable/proportional valves R1, R2 such that if the desired pressure set point is achieved, the steady state air consumption is minimized to meet the flow capacity of the compressor and the vacuum source. It is only when the pressure in the chamber 10 needs to be changed that an air flow is applied. Once the pressure is reached the valves R1, R2 can be closed such that the positive pressure source 24 (e.g. fed by a compressor) and negative pressure source 22 (e.g. fed by a pump) can maintain the respective pressure levels (even the compressor and/or pump can be turned off or operated at a lower power consumption level).

The pressure control unit 21 of the present invention may further comprise one or more air filters 29a, 29b configured to filtrate air that during operation may come into contact with the surgical fluid F in the chamber 10. In an exemplary embodiment, the pressure control unit 21 comprises a first air filter 29a that can be arranged in communication with the main port 25c of the adjustable valve arrangement 25 (as shown in FIGS. 4A and 4B also in direct communication with the chamber 10, e.g. the upper part 10a thereof). As shown in FIGS. 4A, 4B, the first air filter 29a may be arranged in a conduit extending between the main port 25c and the upper part 10a of chamber 10. The first air filter 29a is adapted to filtrate air entering the chamber 10 from the main port 25c and maintains appropriate sterility of the surgical fluid F within the chamber 10. Appropriate sterility of the fluid F can be achieved through an embodiment wherein the first air filter 29a is a bacterial filter (e.g. 0.22 μm bacterial filters). This is useful in irrigation procedures in which the fluid from the chamber 10 is delivered to the eye 1, but this also ensures appropriate sterility of backflush during aspiration procedures (which means irrigation for the aspiration line).

There are several ways in which the first air filter 29a can be arranged within the pressure control unit 21. For example, in an embodiment the pressure sensor 30 may be connected to a conduit extending between the main port 25c and the chamber 10 (also see FIGS. 1 and 2), wherein the first air filter 29a is arranged in the conduit between the pressure sensor 30 and main port 25c. In an alternative embodiment the first air filter 29a is arranged in the conduit between the pressure sensor 30 and the chamber 10.

According to the present invention, the adjustable valve arrangement 25 allows for rapid and accurate control of negative and positive air pressure within the chamber 10. To allow this fast pressure changes, short term mass flow rates are required. To be capable of providing these flow rates that might not match the flow capacity of the internal system pressure sources 22, 24, a vacuum buffer 28a and a pressure buffer 28b are used. Furthermore, fast changes in air pressure can induce short bursts of relatively high mass flow rates and pressure ripples through the pressure control unit 21. To provide dampening of such high mass flow rates and pressure ripples there is provided an embodiment wherein the pressure control unit 21 comprises a vacuum buffer 28a (e.g. a vacuum buffer tank) arranged between the negative pressure source 22 and the vacuum port 25a. In another embodiment a pressure buffer 28b (e.g. pressure buffer tank) may be provided and arranged between the positive pressure source 24 and the pressure port 25b. Of course, in an advantageous embodiment the pressure control unit 21 comprises both the vacuum buffer 28a and the pressure buffer 28b, so that mass flow bursts to and from the chamber 10 are dampened. The vacuum buffer 28a and the pressure buffer 28b each provide capacitance to momentarily absorb/store some of the mass flow rate from/to the chamber 10 and in doing so provide dampening of pressure ripples within the chamber 10. It is noted that either the vacuum buffer 28a and/or the pressure buffer 28b may alternatively or additionally be formed by using the air volume within the pneumatic tubing between the negative/positive pressure sources 22, 24 and the main port 25c.

Because the adjustable valve arrangement 25 allows for rapid changes in pressure within the chamber 10, high pressure pulses may occur within the pressure control unit 21 during operation. Then to ensure operational safety (e.g. in case of failure of the control unit 21 or one or more of the pneumatic components), the adjustable valve arrangement 25 may further comprise one or more safety valves. In an exemplary embodiment, the adjustable valve arrangement 25 comprises a first safety valve configured for venting air to the ambient environment when a particular positive pressure is exceeded. In a further embodiment, the adjustable valve arrangement 25 comprises a second safety valve configured to block air flowing toward and/or from the chamber 10 when a particular negative pressure and/or positive pressure is exceeded within the chamber 10 to avoid damaging the ophthalmic surgical system. Advantageously, the adjustable valve arrangement 25 may comprise both the first and second safety valves for increased safety.

The skilled person will appreciate that in addition to maintaining the chamber pressure at a desired constant level, the pressure control unit 21 described herein may also allow for precise control of the chamber pressure according to a varying pressure profile (e.g. varying aspiration pressure according to a particular aspiration strategy). The arrangements shown in FIGS. 4A and 4B also minimize air consumption within the system, thereby eliminating the need for an external air source to maintain chamber pressure at the desired level.

An important advantage of the pressure control unit 21 of the present invention is that through the main port 25c it is easily connected to an existing chamber 10, such as a disposable chamber, of an ophthalmic aspiration/irrigation system 100, 200. In this way an existing ophthalmic surgical system can deploy the pressure control unit 21 for increasing irrigation and/or aspiration response times as well as increased accuracy at which required pressures can be provided within chamber 10.

However, there may exist cases wherein an existing chamber 10 exhibits specific features or shortcomings that do not allow the pressure control unit 21 to be used for such a chamber 10. In view of these difficulties the pressure control unit 21 comprises the chamber 10 as an integral part thereof. So according to the present invention, the pressure control unit 21 for an ophthalmic irrigation/aspiration system may comprise a negative pressure source 22, a positive pressure source 24 and an adjustable valve arrangement 25, wherein the adjustable valve arrangement 25 comprises a vacuum port 25a connected to the negative pressure source 22 and a pressure port 25b connected to the positive pressure source 24. The adjustable valve arrangement 25 also comprises a main port 25c in controllable fluid communication with the vacuum port 25a and the pressure port 25b. Then the pressure control unit 21 further comprises a chamber 10 configured for exchanging a surgical fluid F. The chamber 10 comprises an upper part 10a for storing air A and a lower part 10b for storing the surgical fluid F to be irrigated or aspirated. The main port 25c of the adjustable valve arrangement 25 is then connected to the chamber 10, in particular the upper part 10a of the chamber 10.

The skilled person in the art will appreciate that all embodiments already described above for the pressure control unit 21 are readily applicable to the pressure control unit 21 in case the chamber 10 is provided as an integral part of the pressure control unit 21. So the adjustable valve arrangement 25 may be a proportionally adjustable (or PWM controlled on/off) valve arrangement to allow for continuous and accurate control of air flow toward and from the chamber 10. In a particular embodiment, the adjustable valve arrangement 25 may comprises a first adjustable valve R1 connected between the vacuum port 25a and the main port 25c and a second adjustable valve R2 connected between the pressure port 25b and the main port 25c. Note that it is also possible that adjustable valve arrangement 25 is a three-way valve arrangement T as depicted in FIG. 4B.

As described earlier, the pressure control unit 21 may comprise a pressure sensor 30 in communication with the main port 25c to monitor the pressure in the chamber 10 and to control the negative and/or positive pressure based on the measured pressure. In a particular embodiment the pressure sensor 30 may be connected to a conduit extending between the main port 25c and the chamber 10, i.e. the upper part 10a thereof. In an alternative embodiment the pressure sensor 30 may be directly connected to the upper part 10a of the chamber 10 for having a more direct measurement of the pressure within the chamber 10. For maintaining a sterile and/or clean surgical fluid F in the chamber 10 during use, there is an embodiment wherein the pressure control unit 21 comprises a pressure sensor 30 directly connected to the upper part 10a of the chamber 10 and wherein a second air filter 29b is arranged between the pressure sensor 30 and the chamber 10. This second filter 29b may be a bacterial filter to specifically maintain sterility of the surgical fluid F. Furthermore, the second filter 29b (e.g. a bacterial filter) in combination with a direct connection to the chamber 10 (instead of via the main port 25c) may be adapted to ensure high dynamic response of the pressure sensor 30 through minimizing air mass flow.

In some embodiments, the chamber 10 has a small air volume (i.e. less than 10 cc). However, the skilled person understands that the chamber 10 may have any air volume for which the control is needed. Note that the air volume is the volume of air within the chamber 10 during normal operation, i.e. when the chamber 10 is filled with fluid within the target range. The target volume of fluid may be 10-15 cc. which would still allow a fast priming (i.e. filling the cassette 8 and all connecting lines with fluid). The variation in amount of fluid in the chamber 10 during normal operation is e.g. about 1 cc, which would also still enable proper and accurate level sensing using the fluid level indicator 50. In an exemplary embodiment, the total internal volume of the chamber 10 is about 25-30 cc.

With reference to FIGS. 1-3, 4A and 4B, in a further aspect the present invention relates to a method for regulating the pressure in an ophthalmic aspiration/irrigation system. In light of the pressure control unit 21 as described above, the pressure in the chamber 10 is regulated by the adjustable valve arrangement 25 which allows for accurate control of the amount of negative pressure from the negative pressure source 22 and the amount of the positive pressure from the positive pressure source 24 at the main ports 25c to reach a required pressure within the chamber 10.

According to the present invention, the method for regulating the pressure in an ophthalmic aspiration/irrigation system comprises a chamber 10 configured for exchanging surgical fluid F and a pressure control unit 21 comprising a negative pressure source 22, a positive pressure source 24 and an adjustable valve arrangement 25, the valve arrangement 25 comprising a vacuum port 25a connected to the negative pressure source 22 and a pressure port 25b connected to the positive pressure source 24, and wherein the valve arrangement 25 further comprises a main port 25c configured for fluid connection to the chamber 10. The method comprises the steps of:

determining a desired chamber pressure;
delivering the desired pressure to the chamber via the main port 25c;
measuring the pressure within the chamber 10; and
adjusting the adjustable valve arrangement 25 to deliver positive or negative pressure to maintain the desired pressure within the chamber 10 based on the measured pressure within the chamber.

The method of the present invention allows the pressure in the chamber 10 to be controlled by both a negative pressure source 22 as well as a positive pressure source 24 through the adjustable valve arrangement 25. This allows for extremely fast and accurate changes in chamber pressure and thus improving overall responsiveness of an ophthalmic aspiration/irrigation system. Furthermore, controlling both the negative and positive pressure sources 22, 24 to maintain desired pressures within the chamber 10 allows non-linearities and/or hysteresis phenomena of an ophthalmic surgical system to be mitigated.

The invention claimed is:

1. A pressure control unit for an ophthalmic aspiration/irrigation system having a chamber with an upper part for storing air and a lower part for storing a surgical fluid to be irrigated or aspirated, the pressure control unit comprising:
a negative pressure source, a positive pressure source and an adjustable valve arrangement, wherein the adjustable valve arrangement comprises a vacuum port connected to the negative pressure source and a pressure port connected to the positive pressure source, and
wherein the adjustable valve arrangement further comprises a main port in controllable fluid communication with the vacuum port and the pressure port, wherein the main port is connectable to the chamber, the adjustable valve arrangement configured to deliver a blend of the negative pressure from the negative pressure source and the positive pressure from the positive pressure source, to the surgical fluid (F) in the chamber, wherein the adjustable valve arrangement comprises a first adjustable valve connected between the vacuum port and the main port and a second adjustable valve connected between the pressure port and the main port, and wherein the first adjustable valve and the second adjustable valve are configured to receive a current, and wherein the first adjustable valve and the second adjustable valve remain closed if the current is below a threshold current.

2. The pressure control unit according to claim 1, wherein the adjustable valve arrangement is a proportionally adjustable valve arrangement.

3. The pressure control unit according to claim 1, wherein the first adjustable valve is a first proportional valve and wherein the second adjustable valve is a second proportional valve.

4. The pressure control unit according to claim 1, wherein the adjustable valve arrangement is a three-way valve arrangement.

5. The pressure control unit according to claim 1, further comprising a vacuum buffer arranged between the negative pressure source and the vacuum port and/or a pressure buffer arranged between the positive pressure source and the pressure port.

6. The pressure control unit according to claim 1, further comprising a flow sensor arranged in a bias flow path between the negative pressure source and the positive pressure source.

7. The pressure control unit according to claim 1, further comprising a first air filter arranged in communication with the main port of the adjustable valve arrangement.

8. The pressure control unit according to claim 7, wherein the first air filter is a bacterial filter.

9. The pressure control unit according to claim 1, further comprising a pressure sensor in communication with the main port.

10. The pressure control unit according to claim 9, further comprising a controller configured to adjust the adjustable valve arrangement to maintain a desired pressure in the chamber in response to the pressure measured by the pressure sensor.

11. The pressure control unit according to claim 1, wherein the negative pressure source and/or the positive pressure source comprise a membrane pump.

12. The pressure control unit according to claim 1, wherein the adjustable valve arrangement comprises one or more safety valves.

13. The pressure control unit according to claim 1, wherein the adjustable valve arrangement is electrically controlled by a current source.

14. A method for regulating pressure in an ophthalmic aspiration/irrigation system comprising a chamber configured for exchanging surgical fluid and a pressure control unit comprising a negative pressure source, a positive pressure source and an adjustable valve arrangement, the adjustable valve arrangement comprising a vacuum port connected to the negative pressure source and a pressure port connected to the positive pressure source, and wherein the valve arrangement further comprises a main port configured for fluid connection to the chamber; wherein the method comprises the steps of: determining a desired chamber pressure; delivering the desired pressure to the chamber via the main port; measuring the pressure within the chamber; and adjusting the adjustable valve arrangement to deliver a blend of the negative pressure from the negative pressure source and of the positive pressure from the positive pressure source, to the surgical fluid (F) in the chamber to maintain the desired pressure within the chamber, wherein the adjustable valve arrangement comprises a first adjustable valve connected between the vacuum port and the main port and a second adjustable valve connected between the pressure port and the main port, and wherein the first adjustable valve and the second adjustable valve are configured to receive a current, and wherein the first adjustable valve and the second adjustable valve remain closed if the current is below a threshold current.

* * * * *